(12) United States Patent
Thornton

(10) Patent No.: US 9,622,836 B2
(45) Date of Patent: *Apr. 18, 2017

(54) DEVICES, SYSTEMS, AND METHODS FOR ORTHODONTIC HARDWARE

(71) Applicant: Justin D. Thornton, North Logan, UT (US)

(72) Inventor: Justin D. Thornton, North Logan, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/805,301

(22) Filed: Jul. 21, 2015

(65) Prior Publication Data

US 2016/0000528 A1    Jan. 7, 2016

Related U.S. Application Data

(63) Continuation of application No. 13/747,790, filed on Jan. 23, 2013, now Pat. No. 9,113,983.

(60) Provisional application No. 61/589,485, filed on Jan. 23, 2012, provisional application No. 61/703,764, filed on Sep. 20, 2012.

(51) Int. Cl.
| | |
|---|---|
| *A61C 7/14* | (2006.01) |
| *A61C 7/12* | (2006.01) |
| *A61C 5/00* | (2017.01) |
| *A61C 13/271* | (2006.01) |
| *A61C 19/06* | (2006.01) |
| *A61M 19/00* | (2006.01) |

(52) U.S. Cl.
CPC .............. *A61C 7/125* (2013.01); *A61C 5/002* (2013.01); *A61C 7/14* (2013.01); *A61C 13/26* (2013.01); *A61C 19/063* (2013.01); *A61M 19/00* (2013.01); *A61M 2210/0637* (2013.01)

(58) Field of Classification Search
CPC .................................. A61C 7/125; A61C 7/14
See application file for complete search history.

(56) References Cited

U.S. PATENT DOCUMENTS

| | | | |
|---|---|---|---|
| 3,505,736 A | | 4/1970 | Brader et al. |
| 4,279,593 A | * | 7/1981 | Rohlcke .................. A61C 7/125 433/8 |
| 4,512,740 A | * | 4/1985 | Kurz ........................ A61C 7/12 433/22 |
| 4,527,975 A | | 7/1985 | Ghafari et al. |
| 4,559,013 A | | 12/1985 | Amstutz et al. |
| 4,609,348 A | | 9/1986 | Rowland |
| 4,913,654 A | | 4/1990 | Morgan et al. |
| 4,978,391 A | | 12/1990 | Jones |
| 5,037,296 A | | 8/1991 | Karwoski |
| 5,160,260 A | | 11/1992 | Chang |
| 5,240,413 A | | 8/1993 | Ashinoff |

(Continued)

*Primary Examiner* — Ralph Lewis
(74) *Attorney, Agent, or Firm* — David L. Stott

(57) ABSTRACT

An appliance for orthodontic hardware in the form of a cap sized to fit over a bracket and arch wire braces system. The cap includes a hollowed, mound shaped body with a bottom edge defining an opening on one side of the body. The cap also includes multiple tabs extending from the edge and partially over the opening. The bottom edge also defines two channels aligned opposite each other and extending from the bottom edge. With this arrangement, the cap can be positioned over a bracket with the tabs engaging the bracket and retaining the cap thereto while the channels defined in the body prevent the cap from engaging the arch wire.

21 Claims, 7 Drawing Sheets

(56) References Cited

U.S. PATENT DOCUMENTS

| | | |
|---|---|---|
| 5,662,471 A | 9/1997 | Fogerty |
| 5,938,435 A | 8/1999 | Raspino, Jr. |
| 5,954,500 A * | 9/1999 | Spriggs .................. A61C 7/00 128/861 |
| 6,074,674 A | 6/2000 | Jay et al. |
| 6,220,857 B1 | 4/2001 | Abels |
| 6,347,939 B2 | 2/2002 | Abels |
| 6,447,290 B1 | 9/2002 | Williams |
| 7,611,352 B2 | 11/2009 | Abels et al. |
| 7,713,057 B2 | 5/2010 | de Salazar Vinas |
| 7,775,794 B2 | 8/2010 | Duran Von Arx |
| 9,113,983 B2 * | 8/2015 | Thornton ............... A61O 5/002 |

\* cited by examiner

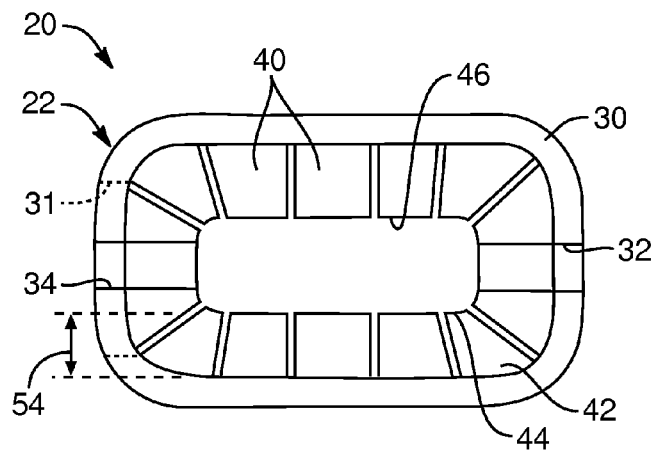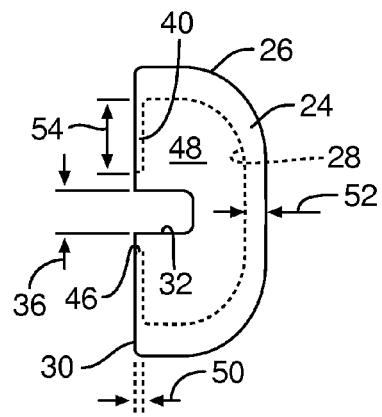
FIG. 2              FIG. 3
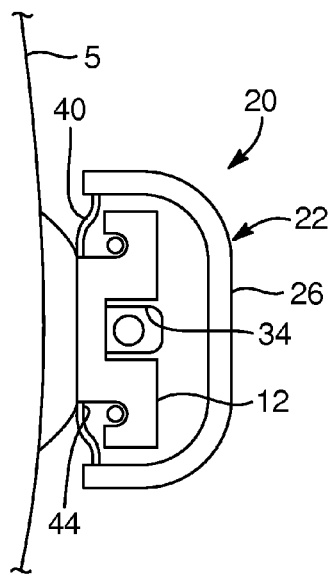
FIG. 4

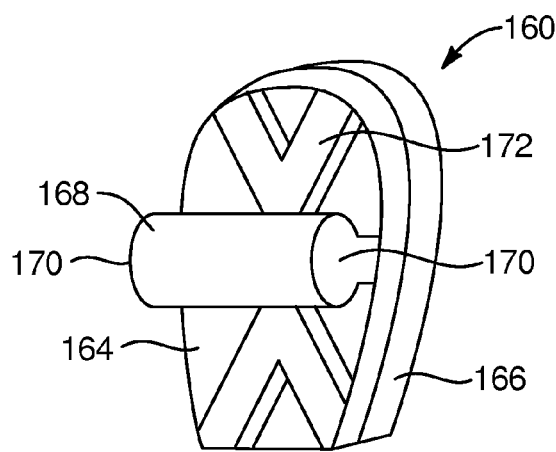
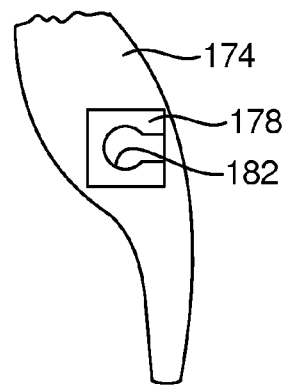
FIG. 12  FIG. 13
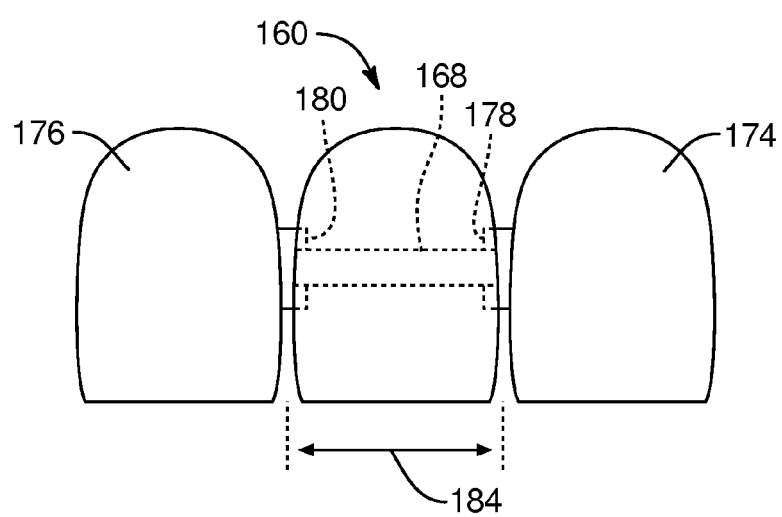
FIG. 14

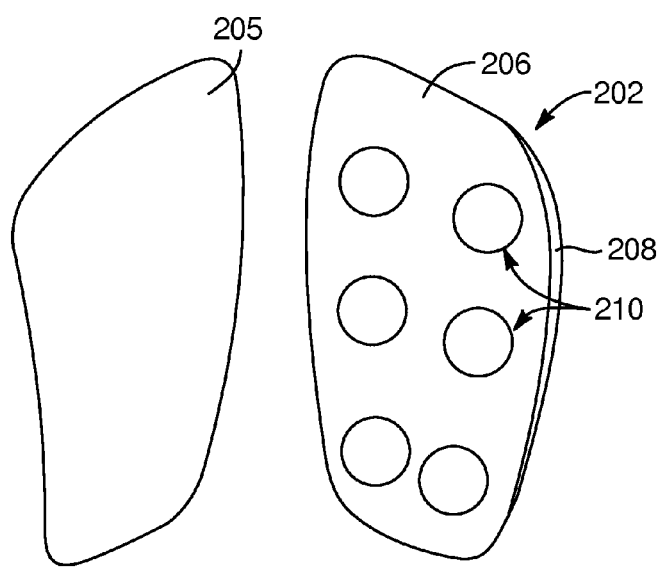
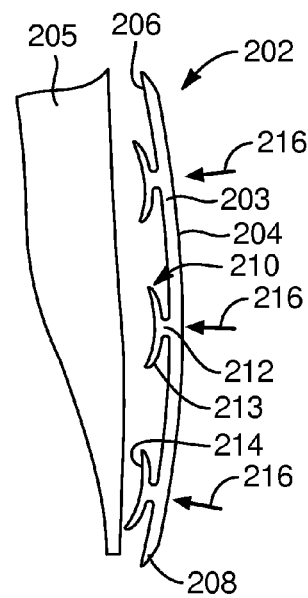
FIG. 15        FIG. 16
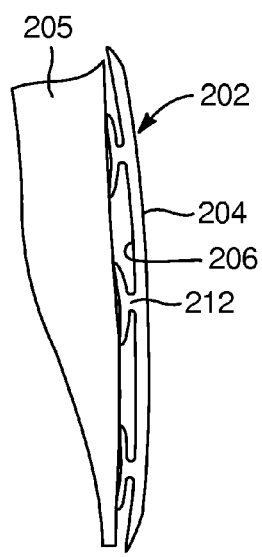
FIG. 17

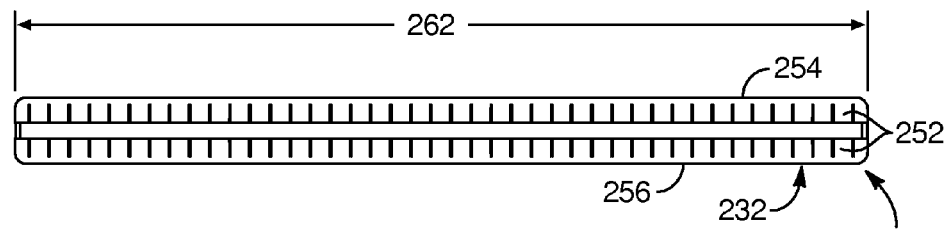
FIG. 18
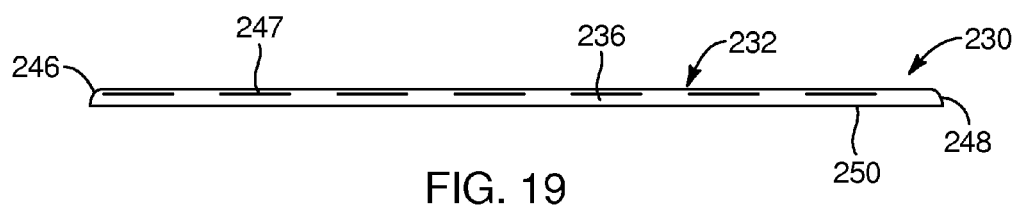
FIG. 19
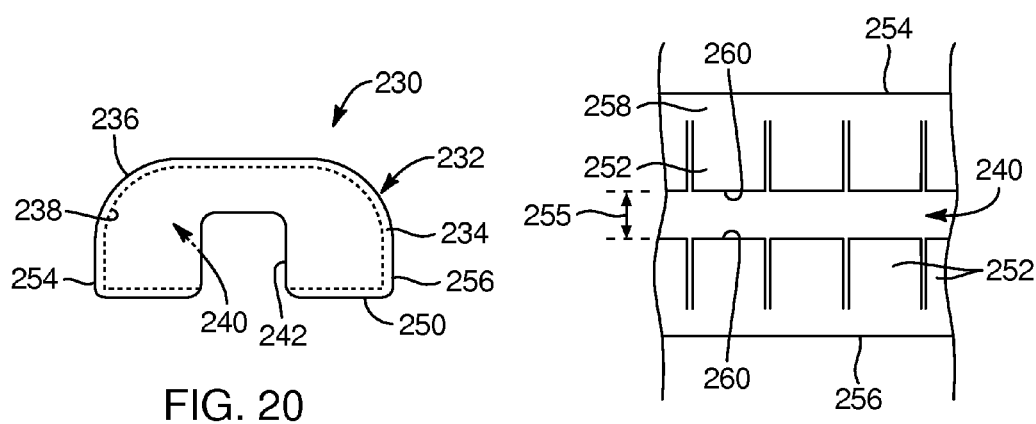
FIG. 20
FIG. 21

US 9,622,836 B2

DEVICES, SYSTEMS, AND METHODS FOR ORTHODONTIC HARDWARE

CROSS-REFERENCE TO RELATED APPLICATIONS

The present application is a continuation of U.S. application Ser. No. 13/747,790, filed Jan. 23, 2013, which claims the benefit of U.S. Provisional Application No. 61/589,485, filed Jan. 23, 2012, and U.S. Provisional Application No. 61/703,764, filed Sep. 20, 2012, the contents of each of which are incorporated by reference herein in their entireties.

TECHNICAL FIELD

The present invention relates generally to appliances for orthodontic hardware and/or teeth. More specifically, the present invention relates to devices, systems and methods for shielding orthodontic hardware and/or deficiencies in one's teeth.

BACKGROUND

Orthodontic braces are designed to align and straighten teeth and position the teeth in regard to a person's bite as a result of force and pressure on the teeth. The primary components needed to help move the teeth, in the case of traditional metal or wire braces, are brackets, bonding material, an arch wire, and ligature elastic, otherwise known as an "O-ring." Over a period of time, the teeth move when the arch wire exerts pressure on the brackets and teeth. At times, additional force may be applied in specific directions by using springs or rubber bands. Although braces are an effective tool for ultimately aligning and straightening teeth, some patients are hesitant to employ braces due to financial constraints, the known discomfort and unfavorable appearance of braces, and undergoing the braces process typically taking approximately two and a half years before the braces are removed.

Efforts have been made to minimize the discomfort and unfavorable appearance. Outside the pressure that braces place on a patient's teeth, discomfort is primarily caused by the brackets and the end of the arch wire, each typically causing irritation to the lips, cheeks, gums, and/or tongue and sometimes causing mucosal ulceration. However, the efforts proposed to overcome the discomfort of braces or unfavorable appearance require bracket appliances only employable over specialized brackets, an orthodontist to properly position the appliance over the bracket or arch wire, and appliances that interfere with the arch wire. These issues result in inefficiencies to the patient and are costly.

In addition, due to various factors, such as poor teeth maintenance, limited dentistry and/or orthodontic work, many individuals face issues of tooth loss or the like. Tooth loss is highly conspicuous and unsightly and, due to financial constraints, often times cannot be fixed or addressed appropriately. These individuals may want a temporary resolve that will minimize the unsightly and conspicuous nature of tooth loss.

Therefore, it would be advantageous to develop an orthodontic appliance that can be positioned by oneself over a bracket or arch wire that also minimizes patient discomfort and minimizes the unfavorable appearance of braces. It would also be advantageous for the orthodontic appliance to be adaptable to most any sized bracket while not interfering with the arch wire. In addition, it would be advantageous to provide a device and method that will minimize issues of tooth loss or unsightly teeth.

BRIEF SUMMARY OF THE INVENTION

Embodiments of the present invention are directed to various devices, systems and methods of providing an orthodontic appliance in the mouth for shielding deficiencies in one's teeth and/or protecting portions of the mouth from sharp portions of a braces system. For example, in one embodiment, a cap configured to be captured over a bracket of a bracket system for teeth. The cap includes a mound shaped body and multiple tabs. The mound shaped body includes a rounded outer surface extending to a bottom edge and an inner surface defining a hollow space. The bottom edge defines two channels aligned opposite each other. Further, the two channels extend from the bottom edge into the body. The multiple tabs of the cap each extend inward from the bottom edge and are independently moveable. With this arrangement, the tabs facilitate engagement and retention of the body to the bracket.

In one embodiment, the multiple tabs are resiliently flexible and are moveable from a first, unattached position to a second, attached position, wherein the tabs extend in a substantially common plane in the first, unattached position. Further, in another embodiment, in the second, attached position, the tabs each independently bend relative to structure of the bracket and are each biased toward the first, unattached position such that the tabs retain the body to the bracket. In still another embodiment, the two channels defined in the body include a substantially constant width along their respective length, the width of the two channels being greater than a diameter of an arch wire such that the width of the channels prevent substantially any interference between the body and the arch wire.

In another embodiment, the multiple tabs extend a predetermined distance inward from the bottom edge so as to define a bottom surface. The bottom surface defines an opening such that the opening extends to the hollow space defined by the inner surface of the body. Further, the multiple tabs may include a depth thickness, the depth thickness being less than a thickness of the mound shaped body. In another embodiment, the two channels are defined in the bottom edge of the body and the multiple tabs are sized to prevent interference with an arch wire of the bracket system. The two channels are configured to receive the arch wire upon the body being captured over the bracket.

In one embodiment, the cap further includes a shield portion coupled to the mound shaped body. Such a shield portion is configured to aesthetically shield a tooth.

In accordance with another embodiment of the present invention, a shield system for shielding teeth is provided. The shield system includes a stand-alone bracket and a shield member. The stand-alone bracket is configured to adhesively adhere to a tooth. Further, the stand-alone bracket includes a base portion and an extension. The shield member includes a front portion and a back portion with a pocket defined therebetween. The back portion defines an opening extending to the pocket. Further, the back portion of the shield member is configured to couple to the extension of the stand-alone bracket such that the extension extends through the opening and into the pocket of the shield member.

In one embodiment, the back portion of the shield member includes multiple tabs configured to engage the extension of the stand-alone bracket. In another embodiment, the multiple tabs are separated from each other by slits defined in the back portion of the shield member. In still another embodiment, the multiple tabs each are coupled to the back portion of the shield member and include a free end. Each free end of the tabs collectively define the opening in the back portion of the shield member.

In another embodiment, the stand-alone bracket includes at least one of a polymeric material, a ceramic material, and a metal material. In another embodiment, the shield member includes a polymeric material.

In yet another embodiment, the shield member aesthetically imitates one or more teeth. In another embodiment, the shield member is coupled to another shield member to aesthetically bridge a gap in the teeth.

In accordance with another embodiment of the present invention, a shield system for shielding a gap in one's teeth is provided. The shield system includes a first bracket, a second bracket, and a shield. The first bracket is configured to be coupled to a first tooth and the second bracket is configured to be coupled to a second tooth. Further, the second bracket is configured to be positioned so as to be aligned with the first bracket with the gap between the first bracket and the second bracket. The shield includes a front side and a rear side. The rear side includes a first extension and a second extension configured to be coupled to the first bracket and the second bracket, respectively. With this arrangement, the shield is configured to aesthetically shield the gap in one's teeth.

In accordance with another embodiment of the present invention, an orthodontic appliance configured to be captured on a braces system in the mouth of a patient is provided. The orthodontic appliance includes a rounded body and multiple tabs. The rounded body includes a wall that defines an outer surface and an inner surface. The inner surface defines a hollow portion within the body. The body includes an opening defined in the outer surface and extending to the hollow portion in the body. The multiple tabs each extend inward over the opening. Further, the multiple tabs are independently moveable and configured to engage and capture the body to a portion of the brace system in the mouth.

In one embodiment, the rounded body is sized and configured to be captured over an end of an arch wire of the brace system. In another embodiment, the rounded body includes a bottom edge that defines the opening. The bottom edge also defines a first channel and a second channel aligned opposite each other in the body and extends from the bottom edge. With this arrangement, the rounded body is configured to be captured over a bracket of a brace system such that an arch wire of the brace system is received in the first and second channels without the body interfering with the arch wire.

In accordance with another embodiment of the present invention, a cap member configured to be positioned over multiple in-line brackets of a bracket system for teeth is provided. The cap member includes an elongated body and multiple tabs. The elongated body extends longitudinally between a first end and a second end thereof. The elongated body includes a rounded outer surface extending laterally between a first side and a second side such that each of the first side and the second side extends to an underside of the elongated body and the rounded outer surface. Also, the elongated body includes an inner surface that defines a hollow space therein. The multiple tabs include a first set of tabs and a second set of tabs. The first set of tabs each extend inward from the first side of the elongated body to define the underside along the first side of the elongated body. Similarly, the second set of tabs each extend inward from the second side of the elongated body to define the underside along the second side of the elongated body. Each of the multiple tabs include a base and a free end such that the first set of tabs extend toward the second set of tabs. With this arrangement, the multiple tabs are independently moveable so as to facilitate engagement and retention to multiple in-line brackets along one's upper or lower teeth.

In another embodiment, the first end and the second end of the elongated body include a first channel and a second channel formed in the elongated body. The first channel and the second channel are sized and configured to receive an arch wire that extends through the multiple in-line brackets. In another embodiment, the inner surface that defines the hollow space is configured to receive multiple in-line brackets. In yet another embodiment, the multiple tabs are configured to bend and be retained to an under-side portion of the brackets with an interference type fit.

In another embodiment, the multiple tabs include a conformable flexible material. In still another embodiment, the elongated body includes a polymeric material. In yet another embodiment, the cap member further includes a strip associated with the elongated body. The strip may include an anesthetic and/or a fluoride and/or a flavor.

In accordance with yet another embodiment of the present invention, a shield member for positioning over a tooth is provided. The shield member includes a body portion and one or more suction cups. The body portion includes a front surface and a rear surface with a periphery therebetween, the front surface defined by the periphery and configured to be sized to conceal a face surface of the tooth. The one or more suction cups are at the rear surface of the shield member and the one or more suction cups are configured to suction to the face surface of the tooth to temporarily adhere the body portion over the tooth.

In another embodiment, the concave suction portion comprises a rounded shape. In still another embodiment, the body portion and the one or more suction cups include a polymeric material.

In accordance with another embodiment of the present invention, a method for temporarily capping or covering orthodontic hardware inside a mouth of a patient is provided. The method includes providing a cap member including a body with a rounded outer surface extending to a bottom edge and an inner surface defining a hollow space within the body, the cap member including multiple tabs each extending inward from the bottom edge; positioning the multiple tabs of the cap member against a face surface of at least one bracket of the orthodontic hardware; and forcing the cap member against the face surface of the bracket such that the multiple tabs flex and move to a rear side of the at least one bracket so that the at least one bracket is positioned within the hollow space defined by the cap member to retain the cap member to the at least one bracket.

In another embodiment, the forcing step includes forcing the multiple tabs to bend and facilitate engagement to the at least one bracket such that each tab is independently bendable relative to an adjacent tab. In another embodiment, the positioning step includes orienting the cap member such that channels defined on opposing sides of the bottom edge of the cap member are aligned with an arch wire of the orthodontic hardware, the channels sized and configured to receive the arch wire. In still another embodiment, the positioning step includes positioning the multiple tabs of the cap member against multiple in-line brackets of the orthodontic hardware such that the cap member exhibits an elongated body. In yet another embodiment, the providing step includes providing at least one of an anesthetic, a fluoride, and a flavor in the form of a strip associated with the cap member.

In accordance with another embodiment of the present invention, a method for temporarily shielding a tooth is provided. The method includes providing a shield portion having a front surface and a rear surface with a periphery therebetween, the rear surface including one or more suction cups and the front surface sized and defined by the periphery; positioning the one or more suction cups against the tooth such that the shield portion conceals a face surface of the tooth; and manually pressing the shield portion against the tooth such that the one or more suction cups are drawn to and retained to the face surface of the tooth.

In another embodiment, the method further includes drying the face surface of the tooth prior to the positioning step. In another embodiment, the method further includes moistening the one or more suction cups at the rear surface of the shield portion prior to the positioning step.

BRIEF DESCRIPTION OF THE SEVERAL VIEWS OF THE DRAWINGS

The foregoing and other advantages of the invention will become apparent upon reading the following detailed description and upon reference to the drawings in which:

FIG. 2 is a bottom view of the cap depicting a retention mechanism for the cap, according to one embodiment of the present invention;

FIG. 3 is a side view of the cap, according to another embodiment of the present invention;

FIG. 4 is a cross-sectional view of the cap attached to the bracket of FIG. 1A, according to another embodiment of the present invention;

FIG. 12 is a perspective view of the shield member for shielding gapped teeth, according to another embodiment of the present invention;

FIG. 13 is a side view of a tooth with a bracket coupled thereto, according to another embodiment of the present invention;

FIG. 14 is a front view of two teeth and the shield member coupled between the two teeth, according to another embodiment of the present invention;

FIG. 15 is a perspective view of a shield member having suction cups on a rear surface thereof prior to being attached to a tooth, according to another embodiment of the present invention;

FIGS. 16 and 17 are cross-sectional views of the shield member of FIG. 15, depicting the shield member respectively adjacent to a tooth and attached to the tooth, according to another embodiment of the present invention;

FIG. 18 is a bottom view of a cap member, according to another embodiment of the present invention;

FIG. 19 is a side view of the cap member of FIG. 18, according to another embodiment of the present invention;

FIG. 20 is an enlarged end view of the cap member of FIG. 19, according to another embodiment of the present invention; and FIG. 21 is an enlarged bottom view of the cap member of FIG. 18, depicting the tabs, according to another embodiment of the present invention.

DETAILED DESCRIPTION OF THE INVENTION

Figure 1:
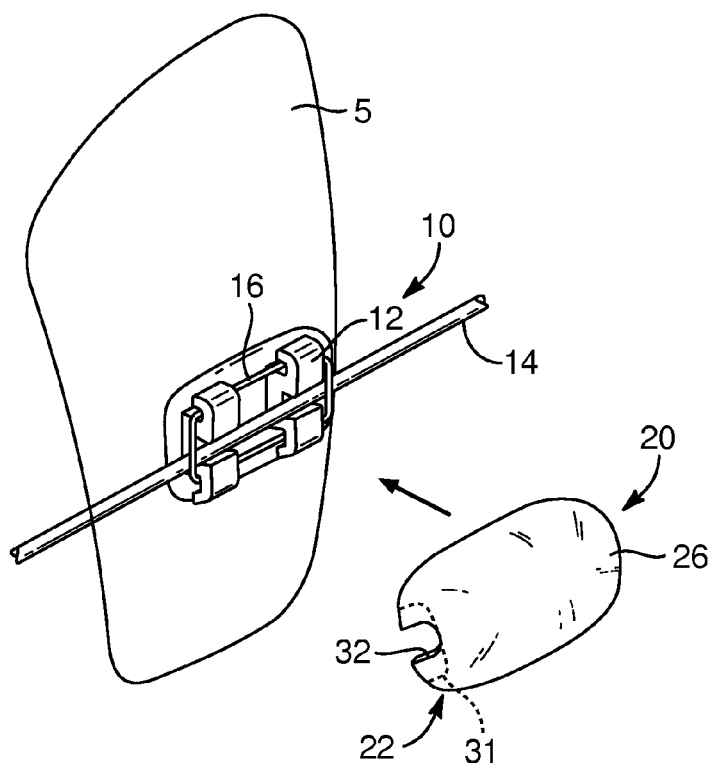
FIG. 1 is a perspective view of an orthodontic appliance or cap sized to fit over a bracket and wire system for teeth, according to an embodiment of the present invention.
Figure 1A:
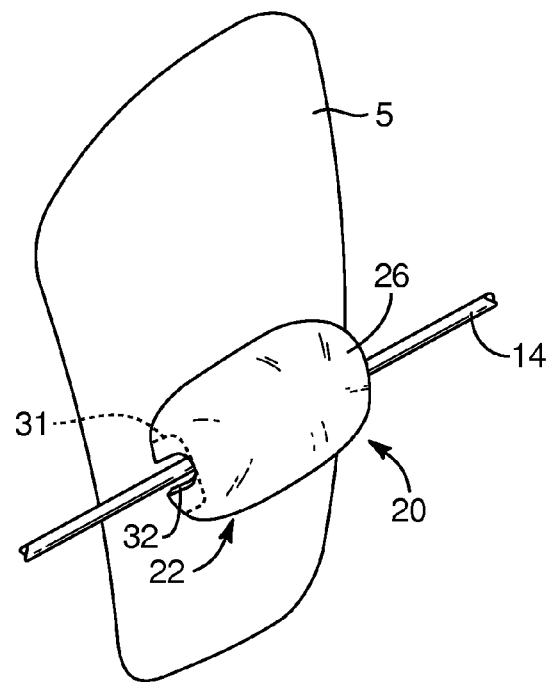
FIG. 1A is a perspective view of the cap captured over the bracket and wire system, according to another embodiment of the present invention.

Referring to FIG. 1, a simplified view of a bracket system 10 or braces system is depicted over a single tooth 5 and a cap 20 in an unattached position. The bracket system 10 may include a bracket 12 coupled and aligned on the teeth with an arch wire 14 or main wire configured to extend through each of the brackets with a ligature wire 16 coupling the arch wire 14 to the bracket 12. The cap 20 may be sized and configured to be captured by the bracket 12 so as to be positioned over the bracket 12, as depicted in FIGS. 1A and 4. Such cap 20 provides a smooth and rounded surface that is non-abrasive to a patient's mouth, such as their lips, cheeks, gums, and tongue. The cap 20 may be formed with one of various shades of white. In another embodiment, the cap 20 may be somewhat transparent.

With respect to FIGS. 1-3, the cap 20, according to one embodiment, may include a rounded body 22 with a mound-like outer shape. The body 22 may include a wall 24 with an outer surface 26 and an inner surface 28 and a bottom edge 30 extending between the outer and inner surfaces 26, 28. The body 22 may include a first channel 32 and a second channel 34 each extending from the bottom edge 30 and into the wall 24 a predetermined distance. The first and second channels 32, 34 extend from the bottom edge 30 at opposite sides of the body 22 and are aligned with each other. The first and second channels 32, 34 may be similarly sized and include a fairly consistently sized gap 36 along their respective length. The gap 36 of the first and second channels 32, 34 is sized and configured to receive the arch wire 14 upon the cap 20 being placed over the bracket 12 such that the cap 20 makes minimal or no contact with the arch wire 14 in the process of positioning the cap 20 as well as in the attached position of the cap 20. As such, the gap 36 of the first and second channels 32, 34 may be larger than the diameter of the arch wire 14. Further, the gap 36 may be much larger so as to expand a majority of the side portion or width of the cap 20 as depicted with broken lines 31 in FIGS. 1, 1A, and 2. Such enlarged gap may be useful for purposes of making the cap, employing molding techniques, such as injection molding, or any other suitable molding technique, as known to one of ordinary skill in the art.

Referring back to FIGS. 1-3, the cap 20 also includes multiple tabs 40. The tabs 40 provide a retention mechanism for the cap 20 to be maintained to the bracket 12. Each tab 40 may include a base 42 and a free end 44, the base 42 being coupled to the bottom edge 30 or to the inner surface 28 adjacent the bottom edge 30 of the body 22. The multiple tabs 40 may extend from the bottom edge 30 of the body 22 in an inward manner such that the tabs 40 extend toward oppositely facing tabs 40. Further, in a first, un-attached position, the tabs 40 generally extend to provide a partial bottom surface of the body 22 and further, extend in a common plane or a substantially flat configuration. Further, the tabs 40 may extend from the bottom edge 30 at their base 42 toward their free end 44 to generally define an opening 46, the opening 46 extending to a hollow space 48 defined by the inner surface 28 of the body 22.

In one embodiment, the tabs 40 may each extend from the bottom edge 30 so as to be separate and distinct from each other. The tabs 40 may be discrete relative to each other in that they may include a slit or gap that separates each tab from an adjacent tab. As such, each tab 40 may independently flex, move and/or bend relative to each other. Further, each tab 40 may independently bend and provide a bias toward the first, un-attached position such that each tab 40 is resiliently flexible. It should be noted that there are no tabs 40 between the first and second channels 32, 34 so that potential interference to the arch wire 14 of the bracket system 10 is limited.

In one embodiment, the tabs 40 may include a depth thickness 50 that may be less than a thickness 52 of the wall 24 of the cap 20. The tabs 40 may also include a similar depth thickness 50 than that of the thickness 52 of the wall 24 of the cap 20. In another embodiment, the tabs may extend a tab length 54 so as to minimize a size of the opening 46 such that one free end 44 of a tab 40 is directly adjacent to an oppositely facing free end 44 of a tab 40. In another embodiment, adjacent tabs 40 may contact each other along the respective tab lengths 54 so as to minimize any slit or gap between adjacently extending tabs 40. In still another embodiment, one tab 40 may slightly over-lap an adjacently extending tab 40 along their respective tab lengths 54 such that the tabs 40 may at least partially flex or move dependent upon an adjacent tab 40 moving or flexing.

As depicted in FIGS. 1A and 4, the cap 20 may be captured over the bracket 12 such that the tabs 40 are placed in a second, attached position. In the second position, the resiliently flexible tabs 40 may be of a length so that the free ends 44 of the tabs 40 may engage with a base of the bracket 12 such that the tabs 40 bias against the base of the bracket 12 in a bent or bunched-up manner, as depicted in FIG. 4. In one embodiment, in the second position, the tabs may be biased toward the first position. The independently bendable tabs 40 provide a retention mechanism that can readily adjust to the variation in structure of an individual bracket 12. Also, the tabs 40 provide for an effective retention mechanism for various bracket configurations. In this manner, the tabs 40 may readily engage the base of the bracket 12 and retain and capture the cap 20 to the bracket 12. Further, since the tabs 40 do not extend over the channels or the space aligned between the first and second channels 32, 34, such arrangement facilitates the body 22 to fit over the bracket 12 so that the arch wire 14 extends through the channels without interference to the arch wire 14 by the tabs 40 or the body in the process of positioning the cap 20 over the bracket 12.

The body 22 and tabs 40 may be formed of a polymeric material, such as silicone, polyethylene, polycarbonate, polypropylene, polyvinyl chloride (PVC), or any other suitable polymeric material or combination of materials. Coatings may also be employed in the manufacture of the cap 20 on various portions, such as the outer surface 26. As known in the art of polymeric materials, the cap 20 may be manufactured employing known techniques, such as extrusion, injection molding, blow molding, thermo-flowing, casting, transfer molding, or any other known manufacturing methods of polymeric materials. The cap 20 may be formed as a seamless unitary structure. The cap 20 may also be formed in multiple components and then attached with known methods.

Figure 5:
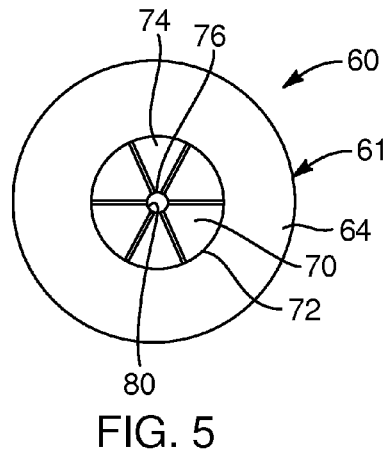
FIG. 5 is a front view of a cap for a wire end extending through braces, according to an embodiment of the present invention.
Figure 6:
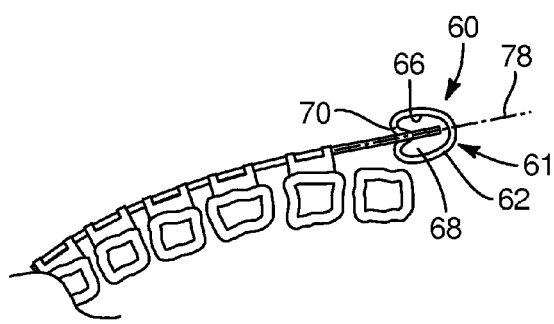
FIG. 6 is a cross-sectional view of the cap attached to the wire end extending through braces, according to one embodiment of the present invention.

Turning now to FIGS. 5 and 6, in another embodiment, a cap 60 may be sized and configured to capture an end 15 of the arch wire 14. The cap 60 in this embodiment may include a spherical or a mound shaped body 61 with a wall 62 having an outer surface 64 and an inner surface 66, the inner surface 66 defining a hollow space 68 in the body 61. Similar to the previous embodiment, the cap 60 may include multiple tabs 70 extending from an edge 72, the edge 72 defined between the outer and inner surfaces 64, 66. Each tab 70 may include a base 74 and a free end 76. The tabs 70 collectively may provide a spoke-like configuration with slits defined between each tab 70. In one embodiment, the free ends 76 of the tabs each may extend toward an axis 78 of the body 61 such that the free ends 76 of the tabs 70 collectively define an opening 80 that extends to the hollow space 68 of the body 61. The tabs 70 may give way to enlarge the opening 80 upon manually pushing the cap 60 over the end 15 of the arch wire 14. Upon the cap 60 being positioned over the wire end 15, the tabs 70 are configured to bias against an outer surface of the arch wire 14 so as to retain or maintain the cap 60 over the wire end 15. With this arrangement, due to the cap 60 having a rounded outer surface 64, the cap 60 minimizes potential irritation and discomfort that would otherwise be caused by the arch wire 14. Such cap 60 may be formed of any suitable polymeric material, such as those described in the previous embodiment, and be formed employing known manufacturing techniques as previously described and known in the art.

Figure 7:
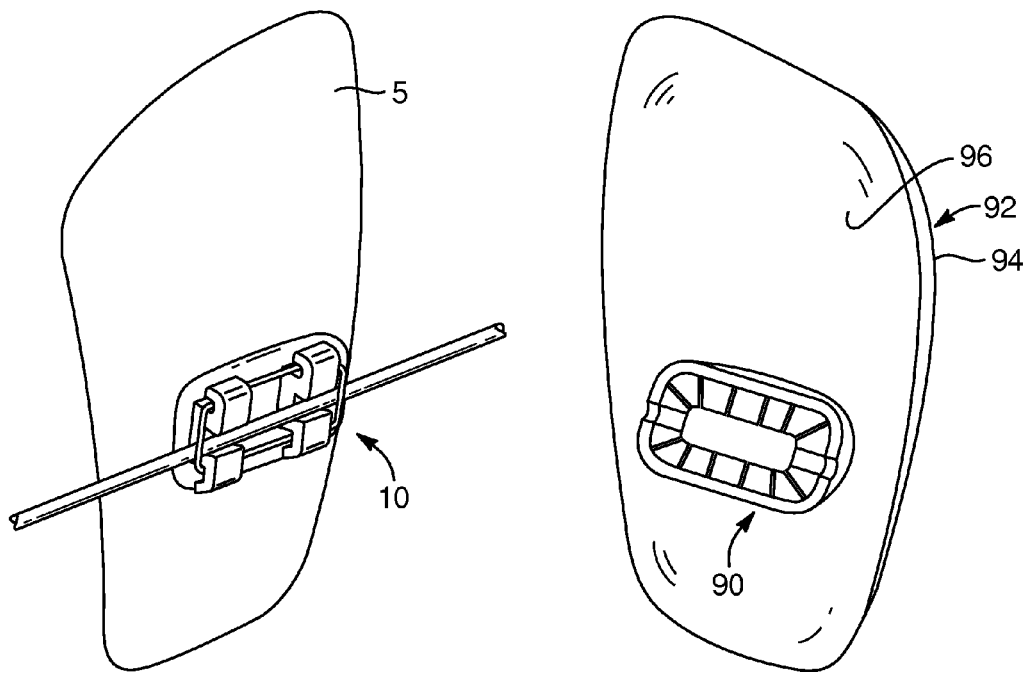
FIG. 7 is a perspective view of a cap and shield member sized to fit over a bracket wire system, according to another embodiment of the present invention.

With respect to FIG. 7, another embodiment of a cap 90 provided over a bracket system 10 is described. This embodiment is similar to the first embodiment describing the cap and bracket system 10 discussed herein (FIGS. 1-4), except this embodiment includes a shield portion 92. The shield portion 92 may be integrally formed, attached, or adhered to a front side of the cap 90. The shield portion 92 may be sized and configured to be positioned over an entire face of a single tooth 5 to substantially and aesthetically shield the braces of a patient. Such shield portion 92 includes a face surface 94 and a back surface 96. The face surface 94 may be a large smooth surface to protect the gums, tongue, and mouth from irritation and discomfort. The back surface 96 is sized and configured to abut at least a portion of the face of the tooth 5.

The cap 90 and shield portion 92 may be formed of any suitable polymeric material as previously set forth herein and be formed employing known manufacturing techniques. In addition, the shield portion 90 may be formed of a more rigid polymeric material, such as polyvinyl, or any other suitable material, such as a ceramic, composites, laminates or combinations thereof. The shield portion 90 may be formed separately from the cap portion and then adhered together with an adhesive. The shield portion and the cap may also be formed as a unitary and seamless structure.

Figures 8, 9:
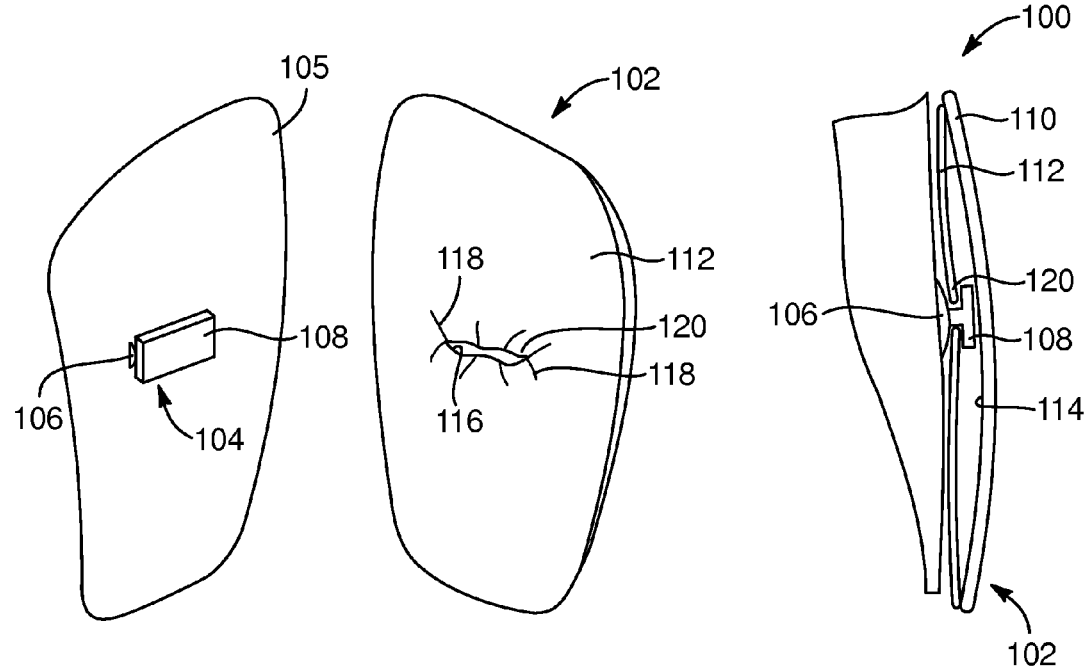
FIG. 8 is a perspective view of a shield member prior to being attached to a bracket coupled to a tooth, according to another embodiment of the present invention.
FIG. 9 is a cross-sectional view of the shield member attached to the bracket depicted in FIG. 8, according to another embodiment of the present invention.

With reference now to FIGS. 8 and 9, a shield system 100 for aesthetically altering the appearance of one's teeth is disclosed. This embodiment provides similar structural characteristics of previous embodiments, however, this embodiment does not include a mound shaped cap. Rather, this embodiment includes a shield member 102 sized and configured to fit over a bracket 104. The bracket 104 may have a lower profile than brackets employed for braces. The bracket 104 is a stand-alone or wireless bracket for temporarily adhering to one's teeth. The bracket 104 of this embodiment may be an attachment mechanism for the shield member 102. The bracket 104 may include a base portion 106 and an extension 108. The base portion 106 may be adhesively adhered to a person's tooth 105. The extension 108 may be configured to correspond with an attachment portion of the shield member 102. The extension 108 may include a square or rectangular configuration or any other suitable configuration sized to correspond and attach to the shield member 102. The bracket 104 of this embodiment may be formed of a polymeric material, ceramic material, or a metallic material, or any combination thereof.

The shield member 102 may include a face portion 110 and a rear portion 112 with a pocket 114 or hollow space disposed and defined therebetween. The rear portion 112 may include an opening 116 defined therein in the form of a horizontal slit or the like. The rear portion 112 may also include vertical and/or transverse slits 118, transverse relative to the opening 116, that define tabs 120 extending toward the opening 116 in the rear portion 112. Such tabs 120 may extend around the opening 116 defined in the rear portion 112. The face portion 110 may include a more rigid material than the rear portion 112. In another embodiment, the face portion 110 and rear portion 112 may be made of a common material, but be formed of different thicknesses so that the face portion 110 is thicker than the rear portion 112 so that the face portion 110 is more rigid than the rear portion 112. The tabs 120 may include structural characteristics to facilitate maintaining the shield member 102 to the bracket 104.

As in previous embodiments, the shield member 102 may be formed of a variety of polymeric materials, such as silicone, polyethylene, polycarbonate, polypropylene, polyvinyl chloride (PVC), polyvinyl, or any other suitable polymeric material or combination of materials, such as polyvinyl for the face portion 110 and silicone for the rear portion 112. As set forth, the face portion 110 of the shield member 102 may be formed of a more rigid material, which may include ceramics, such as porcelain, and various composites and laminates that may include polymeric materials. The shield member 102 may be colored in various shades of white so as to shield any undesired deficiencies in one's teeth.

In another embodiment, the bracket 104 and shield member 102 arrangement may be employed for changing the aesthetic appearance of one's teeth with a shield member 102 that is not colored with various shades of white. For example, the shield member 102 may be gold or black in color. Depending on the color of the shield member 102, such bracket and shield member arrangement may be employed for a myriad of other purposes, such as costume, popular culture, etc.

In still another embodiment, the shield member 102 depicted in FIGS. 8 and 9 may also be employed to shield brackets employed for braces. Such shield member 102 may be employed with a bracket system 10 for braces (See FIG. 1). As such, the opening 116 and tab 120 arrangement defined in the rear portion 112 would be employed similar to the cap discussed herein to engage a bracket for braces and the face portion 110 would provide the advantageous features of protecting one's mouth from discomfort as well as aesthetically shielding the braces. The shield member of this embodiment may provide a lower profile than the embodiment depicted in FIG. 7, for example.

Figures 10, 11:
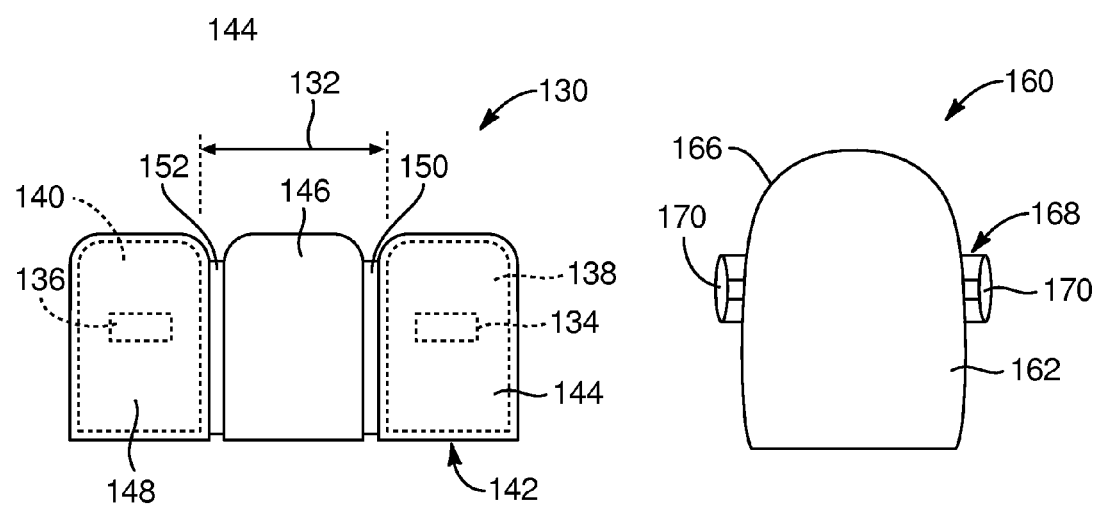
FIG. 10 is a front view of three shield portions attached to two teeth to aesthetically shield the gap in the teeth, according to another embodiment of the present invention.
FIG. 11 is a front view of a shield member for shielding gapped teeth, according to another embodiment of the present invention.

With respect to FIG. 10, in another embodiment, a shield system 130 is disclosed for aesthetically shielding a gap 132 in ones teeth. In this example, the shield system 130 provides for aesthetically shielding deficiencies in one's teeth, such as tooth loss or any other displeasing deficiencies. The shield system 130 may include a first bracket 134 and a second bracket 136 that each may be adhered to a first tooth 138 and a second tooth 140, respectively. The first and second brackets 134, 136 may be similar to the bracket 104 described in FIGS. 8 and 9. The shield system 130 also includes a shield member 142 that may include the aesthetic appearance of three teeth, namely, a first shield portion 144, a second shield portion 146, and a third shield portion 148, the first and second shield portions 144, 146 being joined by a first intermediate portion 150 and the second and third shield portions 146, 148 joined by a second intermediate portion 152. The shield member 142 may include a face portion 154 and a rear portion (not shown). The rear portion may include an opening and tab arrangement (not shown), similar to that described with respect to FIGS. 8 and 9, at the rear portion of the first shield portion 144 and the third shield portion 148. As such, the opening and tab arrangement in the rear portion (not shown) of the first and third shield portions 144, 148 may respectively couple to the first bracket 134 and the second bracket 136 in a similar manner as depicted in the embodiment of FIGS. 8 and 9. With this arrangement, the shield member 142 is retained by the first and third shield portions 144, 148 and the second shield portion 146 aesthetically shields the gap 132 between the first and second tooth 138, 140. The materials employed in this embodiment may be similar to those described in the previous embodiment.

FIGS. 11-14 describe another embodiment for aesthetically shielding a gap 184 or a lost tooth in one's teeth. FIGS. 11-12 depict one embodiment of a shield member 160. The shield member 160 may include a front side 162 and a rear side 164 with an edge extending between the front side 162 and rear side 164 that defines a periphery 166 of the shield member. The rear side 164 may include an extension portion 168 with, for example, two ends 170 sized and configured to couple to respective first and second coupling members 178, 180 (See FIGS. 13 and 14). As depicted in FIG. 11, the extension portion 168 may extend beyond a width or the periphery 166 of the front side 162. Such extension portion 168 may be snipped or cut down to a desired length to match the width for a given gap between teeth. For example, FIG. 12 depicts the extension portion 168 with a longitudinal length (with the ends being snipped) so as to match the approximate width or periphery of the shield member 160. Further, the periphery 166 of the shield member 160 may be cut or filed back to an appropriate size to match the gap 184 (FIG. 14) between one's teeth. Further, the rear side 164 of the shield member 160 may include a backing 172 for additional reinforcement to the shield member 160.

As depicted in FIGS. 13 and 14, the shield member 160 is coupled between a first tooth 174 and a second tooth 176 by coupling the extension portion 168 to a first coupling member 178 and a second coupling member 180. The first and second coupling members 178, 180 may be respectively adhered to an inside surface of the two teeth adjacent to the gap 184. The first and second coupling members 178, 180 each include a coupling configuration that corresponds with a respective end 170 of the extension portion 168. For example, as depicted in FIG. 13, the coupling configuration is a recess 182 formed in the first coupling member 178 that is sized and configured to receive one end 170 of the extension portion 168. The extension portion 168 may be formed of a resilient polymeric material that can properly retain the shield member 160, but can also be readily removed when desired. The front side 162 or front portion of the shield member 160 may be formed of a thin polymeric material. The front side 162 of the shield member 160 may include one of a variety of shades of white that can be matched to one's teeth. With this arrangement, the shield member 160 and first and second coupling members 178, 180 facilitate one to aesthetically shield a the gap 184 in one's teeth.

The first and second coupling members 178, 180 may be formed of a polymeric material, ceramic, or metal, or combinations thereof or any other suitable material as known in the art. The shield member 160 may be formed of one or more materials. For example, the front side 162 and/or the rear side 164 of the shield member 160 may be formed of a polymeric material, similar to those previously set forth, such as polyvinyl, composites, ceramics, laminates or combinations thereof as known by one skilled in the art. Further, the extension portion 168 and backing 172 may be formed of a polymeric material as previously set forth and, preferably, a more compliant polymeric material, such as silicon rubber or the like.

Now with reference to FIGS. 15 through 17, another embodiment of a shield member 202 for purposes of aesthetically shielding one's tooth 205 is provided. Such a shield member 202 may be employed for purposes of shielding the discoloration of one's tooth 205, in which case the shield member may be white or a white-like color to match the other teeth in one's mouth. In another embodiment, the shield member 202 may include a black color or any other color to be employed for, for example, costume purposes.

The shield member includes a body portion 203 having a face surface 204 and a rear surface 206 each defined by a periphery 208. The shield member 202 may include multiple suction cups 210 extending from the rear surface 206. In another embodiment, the shield member 202 may include one suction cup extending from the rear surface 206. Preferably, the shield member 202 may include between two and six suction cups 210, but may exceed six suction cups as the suction cups 210 may be much smaller in comparison to that depicted so as to facilitate additional suction cups. The suction cups 210 may each include a base 212 and a cup portion 213, the cup portion extending from the base with a circular configuration. The base may be centrally located relative to the circular configuration. The base 212 may be in the form of an extension, as depicted, or it may include a low-profile. For example, the base 212 having a low-profile may simply be the interconnection between the cup portion 213 and the rear surface 206 of the shield member 202 such that the rear surface 206 defines one or more concave portions or suction cups therein. Further, each cup portion 213 may include a suctioning surface 214 extending from the base having a concave shape to facilitate effective suctioning of each suction cup 210.

To apply the shield member 202 to a tooth 205, the user may first clean and then dry an outer surface or face surface of the tooth 205. The user may then remove the shield member 202 from its packaging and apply moisture to the suctioning surface 214 of each suction cup 210. Such moistening may be employed with the user's tongue or with a damp cloth. Once the suction cups 210 are moistened, the user may position and align the shield member 202 over a tooth 205 and then apply a force, as indicated by arrow 216, to the face surface 204 of the shield member 202 such that the suctioning surface 214 of one or more suction cups 210 is pressed against the face surface 204 of the tooth 205. In this manner, the suction cups 210 of the shield member 202 become suctioned to the tooth 205 to, thereby, hold the shield member 202 to the tooth and conceal the face surface of the tooth 205.

Such shield member 202, along with the suction cups 210, may be monolithically formed in a unitary and integral manner so as to be a single piece member. In another embodiment, the shield member 202 may be formed separately and with a separate material than the suction cups 210 such that the suction cups are added to the shield member employing various fastening techniques, such as, adhesive, wire fasteners, etc. Further, the shield member 202 may be formed of one or more polymeric materials, ceramics, etc., similar to that described herein for alternate embodiments for a shield member. The suction cups 210 may also be formed with similar polymeric materials or any suitable polymeric material as known to one of ordinary skill in the art that will facilitate effective suctioning of the shield member 202 to one's tooth.

In another embodiment, the suction cups 210 and shield member 202 set forth above may be employed as a shield system similar to the shield system 130 depicted in FIG. 10. For example, at the rear portion or side of a shield system, suction cups may be employed to a first and third shield portion to suction to teeth on both sides of a gap or an unsightly tooth such that a second shield portion extends between the first and third shield portions to hide the gap or unsightly tooth. In this manner, the suction cups may replace the need of adhering temporary stand-alone brackets to the teeth, as set forth and described relative to FIG. 10.

Now with reference to FIGS. 18 through 21, another embodiment of a cap member 230 for positioning over multiple in-line brackets is provided. This embodiment is similar to the cap 20 sized for a single bracket depicted in FIGS. 1 through 4, except in this embodiment, the cap member 230 is sized and configured to engage over multiple in-line brackets of a user's upper teeth or lower teeth.

The cap member 230 may include an elongated body 232 extending between a first end and 246 a second end 248 to define a longitudinal length 262 of the cap member 230. The cap member 230 also may include a wall 234 with an exterior surface 236 and an interior surface 238, the interior surface 238 defining a hollowed portion 240 of the cap member 230. The exterior surface may include a rounded portion (or upper portion) extending laterally between a first side 254 and a second side 256 of the elongated body 232.

The cap member 230 may include a first channel 242 and a second channel (not shown) formed and defined in the wall 234 at the respective first end 246 and the second end 248 of the cap member 230. The channels 242 define a space through which an arch wire 14 may extend upon the cap member 230 being positioned and engaged over and with the brackets 12, similar to that shown in FIGS. 1A and 4.

The cap member 230 may also include an underside 250 with multiple tabs 252 extending from the wall 234 toward each other from the first side 254 and the second side 256 of the cap member 230. For example, the tabs 252 extending from the first side 254 may be a first set of tabs 252 and the tabs 252 extending from the second side 256 may be a second set of tabs 252. Further, the first set of tabs 252 may extend substantially parallel relative to each other. Similarly, the second set of tabs 252 may extend parallel relative to each other. Such tabs 252 may be a continuous extension of the wall 234 at the underside 250 of the cap member 230 such that the tabs 252 each may include a base 258 extending to a free end 260. With this arrangement, the first set of tabs 252 may extend toward the second set of tabs 252 such that there is a gap 255 between the free ends 260 of the first set and the second set of tabs 252. Such a gap 255 may provide clearance to readily receive the in-line brackets into the hollow portion 240 while the tabs 252 engage and grab onto the brackets. The cap member 230 and the tabs 252 may include similar features and structural characteristics as that already described relative to the embodiment depicted in FIGS. 1 through 4, including, but not limited to, wall thickness, tab depth thickness, tab length, etc. Further, the cap member 230 may be formed of similar materials employing similar manufacturing techniques as that described for the cap 20 in the earlier described embodiments.

The cap member 230 of this embodiment may readily be positioned over a set of in-line brackets 12 (See FIGS. 1, 4, and 6) along one's upper or lower teeth and pushed over the brackets 12 so that the brackets are disposed within the hollow portion 240 defined by the interior surface 238 of the cap member 230 with the tabs 252 positioned and engaged with an under or side portion of the bracket 12. As such, along the length 262 of the cap member 230, multiple tabs 252 may be engaging the underside portion of different brackets 12 along the upper or lower teeth with multiple tabs 252 positioned between adjacent brackets that are not engaging a particular bracket along with the arch wire 14 also extending through the hollow portion 240 along the length 262 of the cap member 230. As in the previous embodiments, the tabs 252 may be configured to bias against and hold to the brackets with an interference fit such that the tabs 252 and the free ends 260 thereof may bend and grab to hold and bias against the underside portion of the brackets.

In another embodiment, the cap member 230 may include a shield portion (not shown) extending from the outer or exterior surface 236 of the cap member 230. The shield portion may be similar to the single shield portion depicted and described relative to FIG. 7, except this embodiment may extend along a mid-portion of the cap member and may mimic or correspond with four to six teeth.

In another embodiment, as depicted in FIG. 19, the cap member 230 may include a strip 247 impregnated or imbedded into the body 232 of, for example, the polymeric material. The strip 247 may include an anesthetic base and/or a fluoride base that may include a flavor associated therewith. The flavors may include mint, cherry, strawberry, orange or any other suitable favorable flavor. In another embodiment, the strip 247 may include only one of the above-identified flavors associated with the strip 247 without the base substance of an anesthetic and/or fluoride. In another embodiment, the strip 247 may include only the anesthetic and/or fluoride. The strip 247 may be an elongated, structural strip member that may be embedded into the wall of the cap member 230 along the longitudinal length thereof or the strip 247 may be a chemical substance impregnated into the external surface 236. In one embodiment, the strip 247 may substantially extend along an entire length thereof. In another embodiment, the strip may also extend longitudinally along the length, but as multiple strip pieces, as depicted. In still another embodiment, the strip 247 may be in the form of a thin layer that may be, for example, sprayed, spread, or brushed over the external surface of the cap member 230. The strip 247 may be pre-formed with the cap member 230 or the strip may be applied by the user and come as part of a kit, in which the strip may be applied by spraying or applying such strip from a tube. The strip 247 may be configured to include a time-release such that the strip 247 reacts and releases its flavor, anesthetic, and/or fluoride over a pre-defined period of time. Such time-release may be employed with a particular temperature range or with the mouth's saliva or any other suitable means as known to one of ordinary skill in the art. It should be noted that such a strip 247 may be embodied in the cap 20, 90 described in FIGS. 1 and 7, respectively, or in any other of the embodiments described herein, such as the various shield member embodiments.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention includes all modifications, equivalents, and alternatives falling within the spirit and scope of the invention as defined by the following appended claims.

What is claimed is:

1. A cap configured to be captured to a bracket system for teeth, the cap comprising:
    a body having a wall extending with an outer surface and an inner surface, the inner surface defining a hollow space, the outer surface and the inner surface of the wall extending to a bottom end; and
    multiple tabs each extending inward from the bottom end of the wall, at least one tab of the multiple tabs extending directly alongside and between two adjacent tabs with the at least one tab extending toward another tab that extends from the bottom end at an opposite side of the body, the bottom end at the opposite side of the body including the multiple tabs extending directly alongside and adjacent each other such that each of the multiple tabs extend in a substantially common plane, the multiple tabs being independently moveable relative to each other to collectively cooperate and facilitate engagement and retention of the body to a portion of the bracket system.

2. The cap of claim 1, wherein the bottom end defines two channels aligned opposite each other and extending from the bottom end, the bottom end having a first bottom end and a second bottom end, the first bottom end generally extending parallel relative to the second bottom end.

3. The cap of claim 2, wherein the two channels defined in the bottom end include a substantially constant gap width along their respective length, the gap width of the two channels configured to be greater than a diameter of an arch wire of the bracket system such that the two channels receive the arch wire and substantially prevent any interference between the body and the arch wire.

4. The cap of claim 1, wherein the multiple tabs are resiliently flexible and are moveable from a first, unattached position to a second, attached position, wherein the tabs extend in the substantially common plane in the first, unattached position.

5. The cap of claim 4, wherein, in the second, attached position, the tabs each independently deform relative to structure of the bracket system and are each biased toward the first, unattached position such that the tabs retain the body to the bracket system.

6. The cap of claim 1, wherein the multiple tabs extend a predetermined distance inward from the bottom end so as to define a bottom surface, wherein the bottom surface defines an opening such that the opening extends to the hollow space defined by the inner surface of the body.

7. The cap of claim 1, wherein the multiple tabs include a depth thickness, the depth thickness being less than a thickness of the body.

8. The cap of claim 1, wherein the body is configured to hold at least one of an anesthetic and a fluoride.

9. An orthodontic appliance for temporarily being captured to a bracket system for teeth, the orthodontic appliance comprising:
a body extending with an outer surface and an inner surface to define a wall, the wall extending to a bottom end so as to define a hollow space, the hollow space sized and configured to receive a portion of the brace system; and
multiple tabs each extending inward from the bottom end of the wall, at least one tab of the multiple tabs extending directly alongside and between two adjacent tabs with the at least one tab extending toward another tab that extends from the bottom end at an opposite side of the body, the bottom end at the opposite side of the body including the multiple tabs extending directly alongside and adjacent each other such that each of the multiple tabs extend in a substantially common plane, the multiple tabs being independently movable relative to each other and so that the multiple tabs collectively facilitate engagement and retention of the body to a portion of the bracket system.

10. The orthodontic appliance of claim 9, wherein the bottom end defines two channels aligned opposite each other and extending from the bottom end, the bottom end having a first bottom end and a second bottom end, the first bottom end generally extending parallel relative to the second bottom end.

11. The orthodontic appliance of claim 10, wherein the two channels defined in the bottom end include a substantially constant gap width along their respective length, the gap width of the two channels configured to be greater than a diameter of an arch wire of the bracket system such that the two channels receive the arch wire and substantially prevent any interference between the body and the arch wire.

12. The orthodontic appliance of claim 9, wherein the multiple tabs are resiliently flexible and are moveable from a first, unattached position to a second, attached position, wherein the tabs extend in the substantially common plane in the first, unattached position.

13. The orthodontic appliance of claim 12, wherein, in the second, attached position, the tabs each independently bend relative to structure of the bracket system and are each biased toward the first, unattached position such that the tabs retain the body to the bracket system.

14. The orthodontic appliance of claim 9, wherein the multiple tabs extend a predetermined distance inward from the bottom end so as to define a bottom surface, wherein the bottom surface defines an opening such that the opening extends to the hollow space defined by the inner surface of the body.

15. The orthodontic appliance of claim 9, wherein the multiple tabs include a depth thickness, the depth thickness being less than a thickness of the body.

16. The orthodontic appliance of claim 9, wherein the body is configured to hold at least one of an anesthetic and a fluoride.

17. A method for temporarily covering orthodontic hardware inside a mouth of a patient, the method comprising:
providing a cap body with multiple tabs, the cap body extending with an outer surface and an inner surface to define a wall, the wall extending to a bottom end so as to define a hollow space, the multiple tabs each extending inward from the bottom end of the wall, at least one tab of the multiple tabs extending directly alongside and between two adjacent tabs with the at least one tab extending toward another tab that extends from the bottom end at an opposite side of the body, the bottom end at the opposite side of the body including the multiple tabs extending directly alongside and adjacent each other such that each of the multiple tabs extend in a substantially common plane;
positioning the multiple tabs of the cap body against a portion of the orthodontic hardware; and
forcing the cap body against the portion of the orthodontic hardware such that the multiple tabs independently flex and move over the portion of orthodontic hardware so that the portion of the orthodontic hardware is received within the hollow space defined by the cap body.

18. The method according to claim 17, wherein the forcing comprises forcing the multiple tabs to bend and facilitate engagement to the portion of the orthodontic hardware such that each tab is independently bendable relative to adjacent tabs.

19. The method according to claim 17, wherein the positioning comprises orienting the cap body such that channels defined on opposing sides of the bottom edge of the cap body are aligned with an arch wire of the orthodontic hardware, the channels sized and configured to receive the arch wire.

20. The method according to claim 17, wherein the positioning comprises positioning the multiple tabs of the cap body against multiple in-line brackets of the orthodontic hardware.

21. The method according to claim 17, wherein the providing comprises providing at least one of an anesthetic, a fluoride, and a flavor to the cap body.

* * * * *